United States Patent [19]

Gabetta et al.

[11] Patent Number: 4,863,956

[45] Date of Patent: Sep. 5, 1989

[54] PROCESS FOR OBTAINING PROANTHOCYANIDINE A2, PHARMACEUTICAL COMPOSITIONS AND THEIR THERAPEUTIC USE

[75] Inventors: Bruno Gabetta; Maria J. Magistretti, both of Milan, Italy; Philippe Dostert, Paris, France

[73] Assignees: Inverni Della Beffa SpA, Milan, Italy; Societe de Recherches Industrielles Sori, Paris, France

[21] Appl. No.: 886,790

[22] Filed: Jul. 18, 1986

[30] Foreign Application Priority Data

Jul. 19, 1985 [GB] United Kingdom ............... 8518289

[51] Int. Cl.$^4$ ............................................. A61K 31/35
[52] U.S. Cl. .................................. 514/453; 514/926; 514/927
[58] Field of Search ..................... 514/453, 926, 927

[56] References Cited

U.S. PATENT DOCUMENTS 4,258,055  3/1981  Lietti et al. ..................... 514/456

OTHER PUBLICATIONS

Tetrahedron Lett., 429, 1966.

*Primary Examiner*—Frederick E. Waddell
*Attorney, Agent, or Firm*—Browdy and Neimark

[57] ABSTRACT

There is described a process for preparing proanthocyanidine A2 by extraction from cortex or fruits of *Aesculus hippocastanum* and related species and its activity for stimulating healing processes, e.g. healing wounds and injuries of various origins, gastric and duodenal ulcers for modifying conditions of impaired capillary permeability and resistance and for obtaining an anti-lipid peroxidation effect.

There are also described pharmaceutical formulations suitable for use by topical and systemic routes.

4 Claims, No Drawings

PROCESS FOR OBTAINING PROANTHOCYANIDINE A2, PHARMACEUTICAL COMPOSITIONS AND THEIR THERAPEUTIC USE

The present invention relates to the preparation, the pharmacological activity and the therapeutic application of proanthocyanidine A2 or 8,14-methano-2H,14H-1-benzopyrano[7,8-d][1,3]benzodioxocin-3,5,11,13,15-pentol-2,8-bis(3,4-dihydroxyphenyl)3,4-dihydro[2R-(2α,3α,8β,14β,15R],

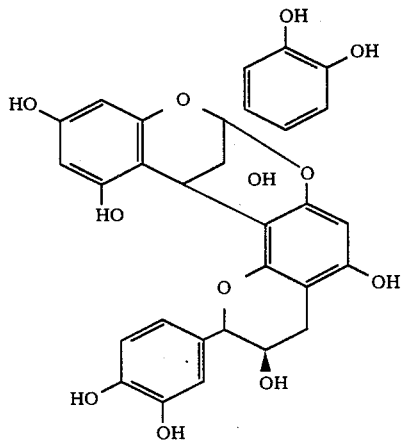
(I)

This compound is usually isolated as a bihydrate and its structure has been defined on the basis of nuclear magnetic resonance (Chem. Commun. 518, 1973) and of circular dichroism (Perkin I, 2375, 1979). It was discovered for the first time in the pericarp of the seeds of *Aesculus hippocastanum* (Tetrahedron Lett., 429, 1966) and has now been isolated by us from branches and cortex of the same tree. Besides proanthocyanidine A2, the cortex and pericarp of the fruits of *Aesculus hippocastanum* contain (−)epicatechin, esculoside, fraxin and polymeric substances of tannic and phlobaphenic nature. Procedures for isolating proanthocyanidine A2 must take account of the presence of these compounds, which are normally more abundant than the desired component, and which possess a polarity very close to that of proanthocyanidine A2.

The present invention relates according to one aspect to the discovery that proanthocyanidine A2 possesses valuable pharmaceutical properties particularly as a cicatrising, cytoprotective, anti-ulcer, veinotonic, vasoprotective and anti-lipid peroxidation agent. Thus one aspect of the present invention comprises the pharmaceutical use of proanthocyanidine A2. Such use may be embodied for example in methods for elliciting a cicatrising and/or cytoprotective and/or vasoprotective and/or anti-ulcer and/or veinotonic and/or anti-lipid peroxidation effect in a subject which comprises administering an effective dose of proanthocyanidine A2. Such use may also be embodied in the industrial application of proanthocyanidine A2 to the manufacture of pharmaceutical compositions.

Thus according to a further aspect of the invention there is provided a method for producing a pharmaceutical composition which comprises bringing proanthocyanidine A2 into a form suitable for therapeutic administration, for example by admixing the proanthocyanidine A2 with a pharmaceutically acceptable diluent or carrier. The invention also provides a pharmaceutical composition comprising proanthocyanidine A2 and a pharmaceutically acceptable diluent or carrier.

The pharmaceutical compositions according to the invention can be in any conventional form suited to the intended mode of administration, i.e. capsules, tablets, pills, dagrees, solutions or suspensions for oral administration, injectable forms, suppositories, vaginal pessaries, ointments, emulsions, dusting powders etc.

The compositions may contain conventional excipients such as starch, talc, lactose, silica, magnesium stearate, zinc oxide, lanolin and flavouring, colouring and perfuming agents.

As will be demonstrated in pharmacological tests reported below, proanthrocyanidine A2 has been found to possess a stimulating action on healing processes which is superior to that of known drugs employed in this field and also a venotonic activity capable for example of normalising conditions of impaired capillary permability and capillary fragility. Proanthocyanidine A2 is particularly active as an anti-ulcer agent useful in the treatment of gastic and duodenal ulcers and as a cytoprotective agent in the prevention of lesions caused by non-steroidal anti-inflammatory agents. They also possess valuable anti-lipid peroxidation activity.

The invention also provides a process for preparing proanthocyanidine A2 which comprises extracting plant tissue obtained from *Aesculus hippocastanum* with a solvent comprising a lower (i.e. C1-4) alkanol (preferably methanol) or a ketone (preferably a lower aliphatic (C3-5) ketone, e.g. acetone), said solvent optionally containing water, and isolating proanthocyanidine A2 from the resulting extract. Optionally the resulting extract is subjected to the following steps:

(a) concentration;
(b) extraction of non-polar substances using a water-immiscible organic solvent in which proanthocyanidine A2 is essentially isoluble;
(c) extraction of proanthocyanidine A2 using a water-immiscible solvent in which proanthocyanidine A2 is soluble.

The product from step (c) may be purified by column chromatography and/or crystallization, preferably both, the crystallization preferably step following the chromatography step.

Advantageously the plant tissue comprises material from the branches and/or cortex, but the cortex and pericarp of the fruit may also be used.

The extracts may be concentrated so as to eliminate the solvent. In the case of extraction with a pure organic solvent, after distillation, the residue of the concentration may be diluted with water in a ratio such as to allow extraction with a water-immiscible organic solvent by liquid/liquid countercurrent extraction in a purification stage. In both cases, before the purification stage, the concentrate is filtered from solid components which are possibly present.

Salts such as NaCl, $NH_4Cl$ and $(NH_4)_2SO_4$ may be added to the solution obtained in this way. Centrifugation for elimination of polymeric tannic substances of various kinds allows the obtained solution to be extracted in a countercurrent fashion with solvents which are immiscible with water, such as halogenated hydrocarbons and other organic solvents, to remove fatty and resinous substances and other undesired lipophilic material. The resulting solution may then be extracted with solvents such as ethyl acetate or with water immiscible alkanols to extract the proanthocyanidine A2 with a high selectivity.

The aqueous phase, from which polyphenols have been removed, may then be eliminated and the combined organic extracts concentrated under vacuum at a temperature not higher than 50° C. to a syrupy consistency. The residue can provide proanthocyanidine A2 by direct crystallisation from water or from water-acetone or water-alcohol solutions, or can be diluted in acetone and filtered through a column of silica gel for the purpose of eliminating oligomeric and polymeric materials. The latter procedure allows proanthocyanidine A2 to be obtained in a high degree of purity after concentration of the solvent and crystallization.

The product obtained according to the method of the present invention may be characterised by its melting point and specific rotation $[\alpha]_D$ and by spectroscopic data such as MS, NMR, UV and IR.

As indicated, in numerous pharmacological tests, proanthocyanidine A2 has revealed a stimulating action on the processes of healing to a degree which is higher than that of known drugs employed in this therapeutic field, and also a venotonic activity normalizing conditions of impaired capillary permeability and capillary fragility. In addition, proanthocyanidine A2 has been shown to possess a strong anti-lipid peroxidation activity.

PHARMACOLOGICAL TESTS

The following tests illustrate selected pharmacological properties of proanthocyanidine A2.

1. Acute Toxicity

The acute toxicity of proanthocyanidine A2 was determined in the mouse and rat on administration by the oral and intreperitoneal routes. The results are given in Table 1:

| Animals | Administration | $LD_{50}$ mg/kg |
|---|---|---|
| Mouse | os | >6000 |
|  | ip | >6000 |
| Rat | os | >6000 |
|  | ip | >3000 |

It can be seen that proanthocyanidine A2 does not exhibit significant acute toxicity following administration by the oral and intraperitoreal routes. The compound also has negligable acute toxicity when administered topically.

2. Cicatrising Activity

The healing activity of proanthocyanidine A2 manifests itself by the topical and also oral route both in normal animals and in animals in which the healing process has been slowed down by treatment with steroids by methods extensively described in literature (Morton J. J. P. et al., Arch Int. Pharmacodyn. 196, 117, 1972).

Tables 2 and 3 give the results of experiments carried out on rats, from which results the favourable effect of the substance on the reduction of the area of wounds is apparent. The triterpene fraction obtained from *Centella asiatica* (CATS), a well-known cicatrizant or healing agent widely used in some European countries, has been chosen as comparison drug.

The stimulating activity on the process of healing has also been demonstrated by other methods, for example by measuring, in mice, the force necessary for breaking a cutaneous scar in the treated animals with respect to the corresponding force in the controls. The method used was that of Sixth et al., Arzneim. Forsch. 18, 1460, 1968. The results are given in Table 4.

TABLE 4
PROANTHOCYANIDIN A2
Activity on wound scar resistance in normal mice by oral route

| Treatment mg/kg | Number of animals | Tension g m + S.E. | Percent increase in comparison |
|---|---|---|---|
| Controls | 20 | 78.55 + 3.50 | |
| Proanthocyanidin A2 100 | 20 | 104.11 + 4.25* | +32.5 |
| Proanthocyanidin A2 200 | 20 | 115.12 + 4.90* | +46.6 |
| CATS 200 | 20 | 101.45 + 3.33* | +29.1 |

*$p < 0.01$

TABLE 2
Proanthocyanidin A2 - Wound healing activity on prednisone treated by topical application.

| Substances | Concentration % | No. of animals | Wound area mm² (m ± s.e.) at days 0 | 1 | 2 | 3 |
|---|---|---|---|---|---|---|
| Controls | — | 10 | 326.12 ± 3.20 | 308.78 ± 3.66** (−10.66) | 292.64 ± 3.54** (−16.12) | 271.12 ± 4.08** (−20.43) |
| Prednisone controls | — | 10 | 326.92 ± 3.20 | 345.62 ± 3.57 | 348.90 ± 3.04 | 340.73 ± 4.23 |
| Proanthocyanidin A2 | 1 | 10 | 324.55 ± 3.77 | 317.39 ± 3.37** (−8.17) | 315.04 ± 3.58** (−9.70) | 308.01 ± 3.77** (−9.60) |
|  | 2 | 10 | 327.71 ± 2.92 | 317.39 ± 3.36 (−8.17) | 305.69 ± 3.89** (−12.38) | 286.62 ± 3.74** (−15.88) |
| C.A.T.S. | 2 | 10 | 326.14 ± 3.63 | 320.32 ± 3.90** (−7.32) | 317.21 ± 3.69** (−9.08) | 312.15 ± 4.00** (−8.38) |

**$p < 0.01$
In brackets percent variations in comparison with prednisone controls.

TABLE 3
Proanthocyanidin A2
wound healing activity by oral route in rats treated with prednisone

| Substances | Dose mg/kg | No. of animals | Surface after 3 days of administrations mm² m ± s.e. |
|---|---|---|---|
| Controls |  | 51 | 287.13 ± 5.26** (−6.99) |
| Prednisone controls |  | 51 | 308.71 ± 4.49 |
| Proanthocyanidin A2 | 50 | 16 | 280.47 ± 7.01* (−9.15) |
|  | 100 | 41 | 271.82 ± 5.35** (−11.95) |
|  | 200 | 51 | 265.88 ± 4.38** (−13.87) |
|  | 400 | 19 | 259.99 ± 7.72** |

TABLE 3-continued

Proanthocyanidin A2 wound healing activity by oral route in rats treated with prednisone

| Substances | Dose mg/kg | No. of animals | Surface after 3 days of administrations mm² m ± s.e. |
|---|---|---|---|
| C.A.T.S. | 200 | 16 | (−15.78) 281.29 ± 6.35* (−8.88) |
|  | 400 | 10 | 284.89 ± 8.96 (−7.72) |

*p < 0.05
**p < 0.01
In brackets percent variations in comparison with prednisone controls.

3. Vaso-protective Activity

In addition to healing activity, proanthocyanidine A2 also possesses a vasotropic activity in terms of modification of capillary permeability and resistance. The latter was evaluated by the method of Charlier R. et al., Arch. Int. Physiol. Bioch. 71-1-1963. The resulting data relating to the protection exerted by proanthocyanidine A2 on conditions of impaired capillary fragility due to vitamin deficiency in rats is given in Table 5.

4. Anti-ulcer Activity

Proanthocyanidine A2 has also proved to be active in ulcer protection tests, as demonstrated by the data given in Table 6. This activity is believed to be a consequence of its healing activity and microcirculation protecting activity.

5. Anti-lipid peroxidation activity

Proanthocyanidine A2 was assayed for anti-lipid peroxidation activity "in vitro" on rat brain homogenate according to the method of Saeed S. A. et al., Biochem. Soc. Trans 9, 442–443, 1981 and on rat hepatic microsomes according to the method of Jha H. C. et al., Biochem. Pharmacol. 34, 1367–1369, 1985. Proanthocyanidine A2, as can be seen from the data in Table 7, strongly inhibited MDA (malondialdehyde) formation, and appeared to be endowed with valuable antiperoxidant activity as well as a low inhibiting activity on NADPH consumption. This activity was confirmed on a rat brain "ex vivo" test.

TABLE 5

Proanthocyanidine A2 - capillary resistance in rats fed on vitamin P deprived diet

| Substances | Oral daily dose mg/kg × 3 days | No. of animals | Percent increase in comparison with controls Time after third administration-hours | | | |
|---|---|---|---|---|---|---|
| | | | 0 | 2 | 4 | 6 |
| Proanthocyanidine A2 | 200 | 8 | 5 | 9** | 9** | 6** |
|  | 400 | 8 | 7 | 15* | 14* | 13* |
| β-Hydroxyethyl-rutosides | 300 | 8 | 8** | 12** | 11** | 10** |

*P < 0.05
**P < 0.01

TABLE 6

Proanthocyanidine A2 - anti-ulcer activity after i.p. administration on ASA induced gastric ulcers in rats

| Substances | Dose mg/kg | No. of animals | Ulceration index (U.I.) mean | Changes in U.I. (1) | No. of stomach without lesions |
|---|---|---|---|---|---|
| Controls | — | 10 | 48,5 | — | 0 |
| Proanthocyanidine A2 | 100 | 10 | 39,6** | −18,4 | 0 |
|  | 200 | 10 | 34,9** | −28,1 | 0 |
|  | 400 | 10 | 28,7*** | −40,8 | 0 |
| CATS | 200 | 10 | 38,7** | −20,2 | 0 |

**P < 0,01;
***P < 0,001;
(1) in comparison with controls

TABLE 7

Proanthocyanidine A2 - "In vitro" inhibition of lipid peroxidation on rat brain homogenate and hepatic microsomes.

| | MDA formation | | | NADPH consumption by hepatic microsomes NADPH 500 μM +Fe²⁺20 μM + ADP 500 μM | |
|---|---|---|---|---|---|
| | brain homogenate IC$_{50}$ (μM) | hepatic microsomes +NADPH +Fe²⁺+ADP IC$_{50}$ (μM) | IC$_{50}$ (hepatic microsomes IC$_{50}$ (brain homogenate) | IC$_{50}$ (μM) | IC$_{50}$ (NADPH) Consumption IC$_{50}$ (MDA Formation) (hepatic microsomes) |
| Proanthocyanidine A2 | 0.45 | 0.8 | 1.8 | 14 | 17.5 |
| Quercetin | 0.9 | 5.1 | 5.7 | 17 | 3.3 |

CLINICAL APPLICATION

On the basis of the above-described pharmacological profile, proanthocyanidine A2 can find use, in suitable pharmaceutical forms, in for example the therapy of bed sores, varices, venous stasis and also in the healing of injuries over large areas of skin due to traumatic burns or lacerations. Its use can also be prescribed in the therapy of gastric and duodenal ulcers to promote the process of repair and in the prevention of the damage produced by non-steroid anti-inflammatory agents.

Solid and liquid pharmaceutical forms such as capsules, tablets, ointments, anhydrous gels, sprinkling powders, phials, etc have been produced for clinical testing of the product. The daily dosage for adult humans of the preparation may vary from 100 to 2000 mg/day according to the type of pathological condition being treated.

The following Examples illustrate the production of proanthocyanidine A2 and its formulation into suitable pharmaceutical forms without, however, limiting the invention in any way.

EXAMPLE 1

Process for preparing proanthocyanidine A2 from cortex of *Aesculus hippocastanum* L.

150 kg of cortex of *Aesculus hippocastanum*, which had been finely ground and previously moistened with 30% v/w of 80% aqueous methanol v/v, are placed in a 1000 l static percolator.

The plant material is extracted with 400 l of 80% aqueous methanol v/v under weak reflux for 4 hours.

Another four extractions with 350 l of 80% aqueous methanol are carried out and the combined percolates are concentrated under vacuum to 150 l at a temperature not higher than 50° C. The concentrate is diluted with 120 l of methanol and centrifuged to eliminate precipitated substances (5 kg) constituted by unwanted materials.

The clarified liquid is subjected to countercurrent extraction with 200 l of chloroform, which permits elimination of 1.5 kg of fatty material, and then with 450 l of ethyl acetate. The aqueous phase is eliminated, while the organic phase, after dehydration with 15 kg of anhydrous $Na_2SO_4$, is concentrated to dryness under vacuum. The residue (8 kg) is taken up in 16 l of acetone. Heating is carried out with weak reflux until complete solubilization is complete, the solution is diluted with 16 l of water and the acetone is eliminated by distillation under vacuum. After standing over night, 1.5 kg of crude proanthocyanidine A2 crystallizes and is recrystallized from 6 l of 50% acqueous acetone.

1.3 kg of proanthocyanidine A2 are obtained which, after recrystallization from water and drying under vacuum at 60° C. for 48 hours, provide 1.1 kg of pure product having the following characteristics:

m.p. >300° C.; $[\alpha]_D$ +63.21 (C=2% in acetone); $E_{1\%}$ at 279 nm in MeOH: 138.5; $M^+$ at m/ 576 ($C_{30}H_{24}O_{12}\cdot 2H_2O$ requires: C, 58.76%; H, 4.57-Found: C, 58.71%; H, 4.63)

EXAMPLE 2

Preparation of proanthocyanidine A2 from cortex of *Aesculus hippocastanum* L.

150 g of cortex of *Aesculus hippocastanum* are extracted in a static percolator by the method described in Example 1. The combined percolates are concentrated under vacuum to 300 l at a temperature not higher than 50° C. 30 kg of NaCl are added under agitation to the turbid concentrate, which is maintained at a temperature of 35° C. Formation of an abundant precipitate occurs which, after decantation and standing over night in a refrigerator, is centrifuged and eliminated. The clarified solution is extracted twice with 100 l of n-hexane. The hexane phase containing fatty substances is eliminated, while the aqueous phase is extracted three times with 50 l of ethyl acetate. After dehydration over $Na_2SO_4$, the organic extracts are concentrated to dryness under vacuum. The residue of 2.4 kg is dissolved in 7.5 l of boiling water and filtration from insoluble residues is carried out. After being left over night in a refrigerator, the filtrate gives 1.4 kg of crude proanthocyanidine A2.

This material is recrystallized from 50% aqueous acetic acid and after filtration, the crystalline solid is washed abundantly with water to complete elimination of the acetic acid. After drying of the product for 48 hours at 60° C. under vacuum, 1.2 kg of pure product having the characteristics of the product prepared in Example 1 are obtained.

EXAMPLE 3

Preparation of proanthocyanidine A2 by a chromatographic process 3 kg of the ethyl acetate extract otained by the method of Example 2 is concentrated to dryness, dissolved in 6 l of anhydrous acetone and absorbed on a chromatographic column containing 60 kg of silica gel (0.02–0.2 mm) which had been stabilized with a hexane/acetone mixture in a ratio of 8:2. On complete absorption of the acetone solution, the column is eluted with a 1:1 acetone/hexane mixture.

The top fractions of the column containing coumarin, (—)epicatechin and other impurities are discarded and those fractions containing proanthocyanidine A2 are collected.

The combined fractions are decolorized with 1% of carbon and concentrated to dryness. The residue is crystallized from 10 volumes of $H_2O$.

After drying, 1.45 kg of pure proantocyanidine A2 are obtained.

PHARMACEUTICAL FORMULATIONS

EXAMPLE 4

Preparation of proanthocyanidine A2 capsules

Each 200 mg capsule contains

| | |
|---|---|
| Proanthocyanidine A2 | 100 mg |
| Lactose | 95 mg |
| Silica powder | 3 mg |
| Magnesium stearate | 1 mg |
| Talc | 1 mg |

EXAMPLE 5

Preparation of a sprinkling powder containing proanthocyanidine A2

Each 100 g of sprinkling powder contain

| | |
|---|---|
| Proanthocyanidine A2 | 2 g |
| Lanolin | 8 g |
| Zinc oxide | 10 g |
| Lavander essence | 1 g |

| | |
|---|---|
| Precipitated silica | 4 g |
| Starch | 15 g |
| Talc | 60 g |

We claim:

1. A pharmaceutical composition for producing a cicatrising effect in a subject requiring stimulation of wound-healing processes, comprising an amount of proanthocyanidine A2 effective to produce a cicatrising effect and a pharmaceutically acceptable excipient.

2. A method of producing a cicatrising effect in a subject requiring stimulation of wound-healing processes, comprising administering to the subject in need thereof an effective amount to produce a cicatrising effect of proanthocyanidine A2.

3. A method according to claim 2 wherein said proanthocyanidine A2 is orally administered at the rate of 100 to 2,000 mg/day.

4. A method of wound healing comprising administering to a subject an amount effective of Proanthocyanidine A2 sufficient to improve the healing of a wound.

* * * * *